United States Patent [19]

Fulton

[11] 3,932,624

[45] Jan. 13, 1976

[54] METHOD FOR PROLONGING THE INHIBITORY EFFECT OF SARALASIN ON ANGIOTENSIN II

[75] Inventor: Robert W. Fulton, Hamilton, N.Y.

[73] Assignee: Morton-Norwich Products, Inc., Norwich, N.Y.

[22] Filed: June 17, 1974

[21] Appl. No.: 479,829

[52] U.S. Cl. ................................. 424/177; 424/360
[51] Int. Cl.[2] .................... A61K 37/00; C07C 103/52
[58] Field of Search .......... 424/177, 360; 260/112.5

[56] References Cited
FOREIGN PATENTS OR APPLICATIONS
2,127,393   9/1972   Germany OTHER PUBLICATIONS
Goodman et al., "Pharmacological Basis of Therapeutics," 2nd Ed., MacMillan Co., New York, 1955, pp. 781–782.

Sollmann, "Manual of Pharmacology," 7th Ed., Saunders Co., Philadelphia, 1948, p. 56.

Brunner et al., Science, 174, 1344–1346 (1971).

Johnson et al., Chem. Abstr. 78:132114k (1973).

Pals et al., Chem. Abstr. 76:81495j (1972).

*Primary Examiner*—Lewis Gotts
*Assistant Examiner*—Reginald J. Suyat
*Attorney, Agent, or Firm*—Anthony J. Franze

[57] ABSTRACT

The angiotensin II inhibition by saralasin is prolonged by its subcutaneous administration in the form of a gel.

1 Claim, No Drawings

METHOD FOR PROLONGING THE INHIBITORY EFFECT OF SARALASIN ON ANGIOTENSIN II

This invention is concerned with pharmaceutical formulation. More particularly it is concerned with the preparation of a gel form of the potent hypotensive agent saralasin.

Saralasin (1-sar-8-L-ala-angiotensin II) is known to inhibit the powerful hypertensive agent angiotensin II upon intravenous infusion to rats and dogs. Unfortunately, its antihypertensive effect is of relatively short duration necessitating continuous infusion, a cumbersome and undesirable therapy tolerated nonetheless because of saralasin's highly potent and specific inhibition of angiotensin II associated with the hypertensive state.

It has been found that the hypotensive effect of saralasin can be potentiated and prolonged by its subcutaneous administration in gel form to animals. The vehicle currently preferred consists of a 15% gelatin solution prepared by dissolving gelatin in sterile physiological saline. Saralasin composed in such a vehicle so that a one milliter portion administered in that or an equally divided amount provides a dose of 5 mg/kg subcutaneously to rats rendered hypertensive through the infusion of angiotensin II in the amount of 2.5 ug/kg/min negates the hypertensive effect of angiotensin II at least twice as long as saralasin similarly administered in physiological saline. For example, at one hundred twenty minutes following the administration of the drug saralasin the percentage of predrug blood pressure is about 69% in the case of the gel form and about 98% in the case of saline form while at two hundred forty minutes post dosing the percentage is about 80% in the case of the gel and 100% in the case of saline. At sixty minutes post dosing the percentage is about 64% in the case of the gel and about 80% in the case of saline.

What is claimed is:

1. The method of prolonging the antihypertensive effect of saralasin to angiotensin II in animals which consists in administering subcutaneously to angiotensin II hypertensive animals a composition consisting of saralasin in a 15% gelatin gel in an amount to deliver a dose of saralasin of about 5 mg/kg.

* * * * *